United States Patent
Jin et al.

(10) Patent No.: US 10,799,215 B2
(45) Date of Patent: Oct. 13, 2020

(54) ULTRASOUND SYSTEMS, METHODS AND APPARATUS FOR ASSOCIATING DETECTION INFORMATION OF THE SAME

(71) Applicant: SHENZHEN MINDRAY BIO-MEDICAL ELECTRONICS CO., LTD., Shenzhen (CN)

(72) Inventors: Meng Jin, Shenzhen (CN); Longfei Cong, Shenzhen (CN); Xiaoping Chen, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 636 days.

(21) Appl. No.: 14/730,035

(22) Filed: Jun. 3, 2015

(65) Prior Publication Data
US 2015/0265248 A1    Sep. 24, 2015

Related U.S. Application Data

(63) Continuation of application No. PCT/CN2013/083882, filed on Sep. 22, 2013.

(30) Foreign Application Priority Data

Dec. 3, 2012   (CN) .......................... 2012 1 0508940

(51) Int. Cl.
*A61B 8/00*   (2006.01)
*A61B 8/08*   (2006.01)
*A61B 8/14*   (2006.01)

(52) U.S. Cl.
CPC ............ *A61B 8/469* (2013.01); *A61B 8/0883* (2013.01); *A61B 8/14* (2013.01); *A61B 8/46* (2013.01);

(Continued)

(58) Field of Classification Search
None
See application file for complete search history.

(56) References Cited

U.S. PATENT DOCUMENTS

2003/0171668 A1*  9/2003  Tsujino ............... A61B 8/0883
                                                      600/407
2005/0043609 A1*  2/2005  Murphy ................ G16H 50/50
                                                      600/408

(Continued)

FOREIGN PATENT DOCUMENTS

CN          1442118      9/2003
CN        101066212     11/2007

(Continued)

*Primary Examiner* — Katherine L Fernandez
(74) *Attorney, Agent, or Firm* — Kory D. Christensen (57) ABSTRACT

Methods for associating detection information of an ultrasound system includes receiving an ROI (region of interest) and an image display type that are selected by an operator on an image detected by the ultrasound system, performing motion tracking for the ROI to obtain tracking information, configuring the image detected by the ultrasound system and position information of the ROI in a first display area of a display device for displaying, configuring quantitative parameter information related to the image in a second display area of the display device for displaying selecting an image model according to the image display type, and configuring the image model in a third display area of the display device for displaying. The methods can display detection information obtained by the ultrasound system on the display device more intuitively.

29 Claims, 4 Drawing Sheets

(52) U.S. Cl.
CPC .............. *A61B 8/463* (2013.01); *A61B 8/464* (2013.01); *A61B 8/485* (2013.01); *A61B 8/523* (2013.01); *A61B 8/5207* (2013.01); *A61B 8/5223* (2013.01); *A61B 8/5276* (2013.01)

(56) References Cited

U.S. PATENT DOCUMENTS

| | | | | |
|---|---|---|---|---|
| 2006/0004291 A1* | 1/2006 | Heimdal | .................. | A61B 8/08 600/459 |
| 2006/0239527 A1* | 10/2006 | Krishnan | .................. | A61B 8/08 382/128 |
| 2007/0016019 A1* | 1/2007 | Salgo | .................... | A61B 5/1075 600/437 |
| 2007/0258631 A1* | 11/2007 | Friedman | .................. | A61B 8/08 382/128 |
| 2011/0313291 A1* | 12/2011 | Chono | ..................... | A61B 8/08 600/440 |
| 2012/0323118 A1* | 12/2012 | Menon Gopalakrishna | ................ | A61B 6/463 600/431 |

FOREIGN PATENT DOCUMENTS

| | | |
|---|---|---|
| CN | 102724918 | 10/2012 |
| JP | 2012029722 | 2/2012 |

\* cited by examiner

ULTRASOUND SYSTEMS, METHODS AND APPARATUS FOR ASSOCIATING DETECTION INFORMATION OF THE SAME

TECHNICAL FIELD

This disclosure relates to medical imaging fields, and particularly to ultrasound systems and methods and apparatuses for associating detection information of the same.

BACKGROUND

Ultrasound systems are capable of obtaining cardiac motion images and parameters. During this process, there is no need to inject any contrast agent, isotope or dye, thereby preventing both patients and doctors from exposure to radiation from radioactive substances. Besides, the ultrasound systems are easy and repeatable in operation, and can be manipulated at a bedside; each chamber of a heart can be examined from multiple planes and multiple dimensions through the ultrasound systems. At present, common echocardiographic examination modes may include a B-mode and a tissue Doppler imaging mode (TDI). The B-mode can be used to obtain dynamic anatomic information of a heart. The doctors can analyze cardiac motion condition according to a movie file obtained under the B-mode. In recent years, motion tracking technology based on speckle tracking technology has become a rapidly growing area for ultrasound imaging. Speckle tracking technology can obtain tissues' position change information by tracking the positions of ultrasonic scattering spots in a B-mode ultrasound image.

When using the speckle tracking technology to track a region of interest, the obtained information can be displayed on a display screen, where varieties of images, charts and text can be used to display the information. The text is usually used for illustrating the image or the chart; for example, an image type can be indicated by virtue of text. In the case where there is too much information to be displayed, it will be difficult for users to perceive the text.

SUMMARY OF THIS DISCLOSURE

This disclosure provides methods and apparatuses for associating detection information in ultrasound systems that can display the information obtained in the ultrasound systems on a display screen in a more intuitive mode.

In one aspect, a method for associating detection information of an ultrasound system may include following steps:

receiving a region of interest and an image display type that are selected by an operator for images detected by the ultrasound system;

performing motion tracking for the region of interest and obtaining tracking information, where the tracking information may include position information of the region of interest in each image, and quantitative parameter information related to the images, where the quantitative parameter information may include quantitative parameter values;

configuring each image detected by the ultrasound system and the position information of the region of interest corresponding to each image in a first display area of a display device for displaying;

configuring the quantitative parameter information related to the images in a second display area of the display device for displaying; and selecting, according to the image display type, an image model corresponding to the images detected by the ultrasound system, and configuring the image model in a third display area of the display device for displaying.

In some embodiments, the method for associating detection information may further include: dividing the region of interest into multiple image segments based on a predetermined segment setting, calculating the quantitative parameter value for each image segment of the region of interest, generating a quantitative parameter curve corresponding to each image segment according to the quantitative parameter values of each image segment and time information of the images corresponding to the quantitative parameter values, and displaying the quantitative parameter curve on the second display area.

In some embodiments, during the display of the image model, the image model is divided into multiple model segments based on a segment number of the predetermined segment setting and each model segment of the image model is filled using different colors, where the quantitative parameter curve also corresponds to each model segment. During the generation of the quantitative parameter curve, color coding is performed for the quantitative parameter curve corresponding to each image segment, wherein the color of the quantitative parameter curve is consistent with that of its corresponding model segment.

In some embodiments, the method for associating detection information may further include receiving a segment selection operation on the image model by the operator, and highlighting or hiding the selected model segment and the quantitative parameter curve corresponding to the selected model segment.

In some embodiments, the method for associating detection information may further include receiving a segment selection operation on the image model by the operator, and hiding an unselected model segment and the quantitative parameter curve corresponding to the unselected model segment.

In some embodiments, the method for associating detection information may further include obtaining a judgment result on a tracking result of each image segment, and displaying a sign corresponding to the judgment result on a corresponding model segment of the image model.

In some embodiments, the method for associating detection information may further include dispersing the region of interest into separated control points, and performing the motion tracking for the control points, wherein the position information of the region of interest comprises position information of the control points.

In another aspect, an apparatus for associating detection information of an ultrasound system may include a motion tracking unit, a tracking result calculation unit and a display configuration unit. The motion tracking unit can receive an image display type and a region of interest that is selected by an operator for images detected by the ultrasound system, and perform motion tracking for the region of interest. The tracking result calculation unit can obtain position information of the region of interest in each image from the motion tracking unit and calculate quantitative parameter information related to the images, where the quantitative parameter information may include quantitative parameter values. The display configuration unit can configure each image detected by the ultrasound system and the position information of the region of interest corresponding to each image in a first display area of a display device for displaying, configure the quantitative parameter information related to the images in a second display area of the display device for displaying, select an image model corresponding to the images according to the image display type, and configure the image model in a third display area of the display device for displaying.

In some embodiments, the display configuration unit can divide the region of interest into multiple image segments based on a predetermined segment setting, calculate the quantitative parameter value for each image segment of the region of interest, generating a quantitative parameter curve corresponding to each image segment according to the quantitative parameter values of each image segment and time information of the images corresponding to the quantitative parameter values, and display the quantitative parameter curve on the second display area.

In some embodiments, the display configuration unit divides the image model into multiple model segments based on a segment number of the predetermined segment setting and fills each model segment of the image model using different colors during the display of the image model, where the quantitative parameter curve also corresponds to each model segment. The display configuration unit performs color coding for the quantitative parameter curve corresponding to each image segment during the generation of the quantitative parameter curve, wherein the color of the quantitative parameter curve is consistent with that of its corresponding model segment.

In some embodiments, the display configuration unit may highlight or hide a selected model segment and the quantitative parameter curve corresponding to the selected model segment based on a segment selection operation performed by the operator on the image model.

In some embodiments, the display configuration unit may hide an unselected model segment and the quantitative parameter curve corresponding to the unselected model segment based on a segment selection operation performed by the operator on the image model.

In some embodiments, the display configuration unit displays a sign that corresponds to a judgment result of a tracking result of each image segment on a corresponding model segment of the image model.

In some embodiments, the images detected by the ultrasound system are cardiac images, and the quantitative parameter comprises velocity, displacement, strain and/or strain rate.

In some embodiments, the motion tracking unit disperses the region of interest into multiple control points and performs the motion tracking for the control points; the position information of the region of interest comprises position information of the control points.

In some embodiments, the quantitative parameter value of each image segment is equal to a weight sum or an average value of the quantitative parameter values of the control points contained in each image segment.

In some embodiments, the position information of the region of interest comprises position information of a border of the region of interest.

In still another aspect, an ultrasound system can include an image acquisition module which may include a transmission module for emitting an ultrasonic wave by an ultrasound probe and a receiving module for receiving echo signals, a beamforming module for processing the echo signals to obtain B-mode ultrasound images, and the above-described apparatus for associating detection information which can perform association processing on the detection information based on the B-mode ultrasound images.

In various embodiments of this disclosure, content that is currently displayed can be identified using icons such as models. Therefore, it can help users to intuitively perceive the content displayed in a current image and reduce difficulties in searching or the possibility of wrong perceptions brought about by any other modes such as text.

BRIEF DESCRIPTION OF THE DRAWINGS

Following detailed descriptions of respective embodiments in this disclosure can be understood better when combining with these figures, in which the same structure is represented by the same reference sign. In the figures.

DETAILED DESCRIPTION

This disclosure is described in detail with reference to drawings and specific implementations below.

Figure 1:
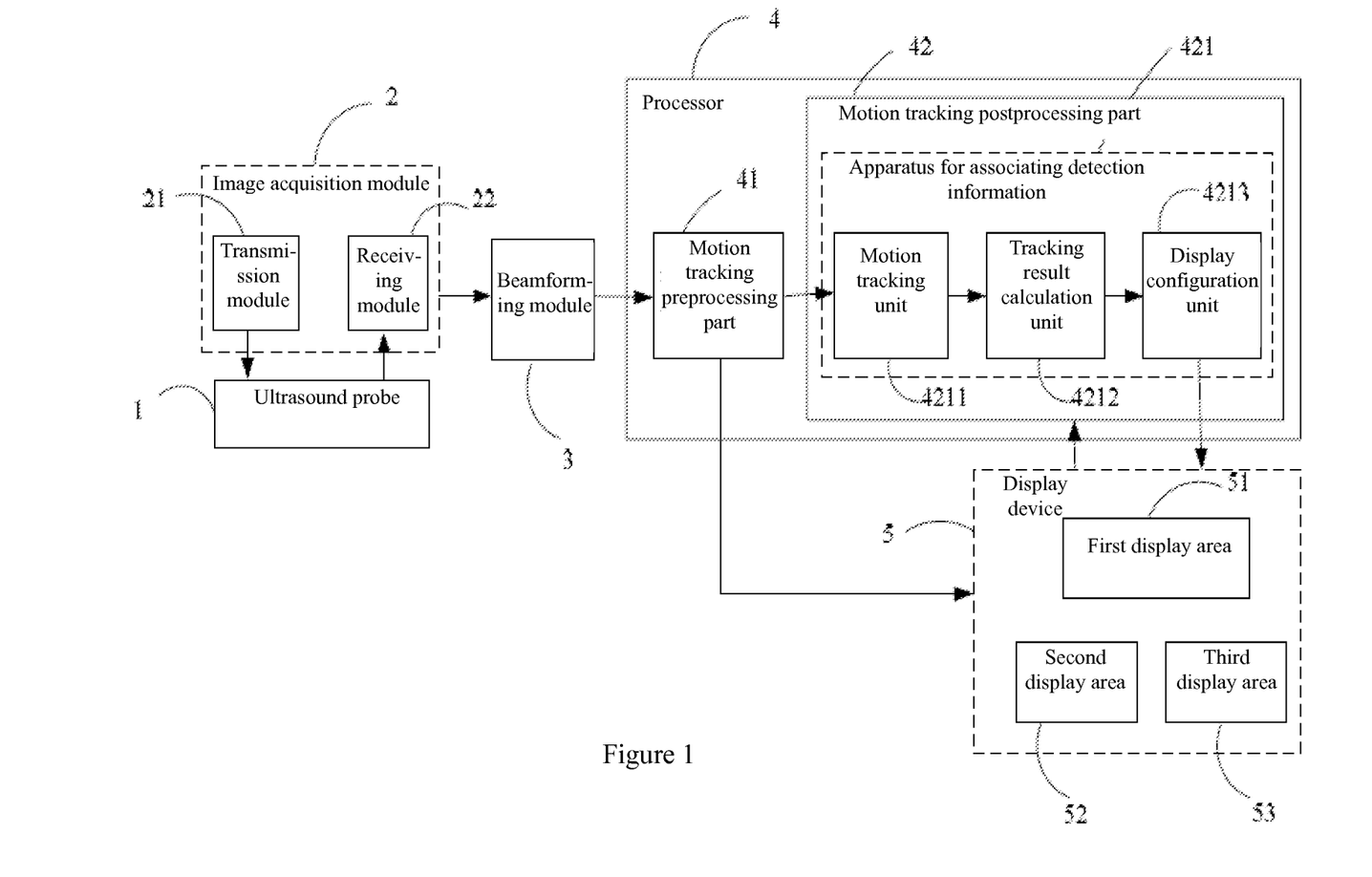
FIG. 1 is a structure diagram for an ultrasound system according to an embodiment of this disclosure.

As shown in FIG. 1, an ultrasound system may include an ultrasound probe 1, an image acquisition module 2, a beamforming module 3, a processor 4 and a display device 5.

The image acquisition module 2 can include a transmission module 21 and a receiving module 22. The transmission module 21 can drive the ultrasound probe 1 (specifically, a transducer) to emit ultrasonic beams in accordance with a selected transmission mode. The ultrasonic probe 1 can have several array elements, each of which is capable of emitting the ultrasonic beams. When an examined subject (such as a patient) is under examination, a surface of the ultrasonic probe 1 may get in touch with skin of the examined subject, and its array elements may emit the ultrasonic beams having a certain frequency into the body of the examined subject. In this way, when an ultrasonic wave emitted from the ultrasound probe 1 enters into the tissue to be examined, the ultrasonic wave can be reflected by the tissue to generate echoes that will return to the ultrasound probe 1, and the echoes can be received by the receiving module 22 and provided to the beamforming module 3 after processing. In embodiments of this disclosure, ultrasound images can be obtained after the processing of the beamforming module 3, the processor 4 may process the ultrasound images, and the display device 5 can display the ultrasound images and other information associated with the images.

Taking a B-mode examination on moving tissues as an example, B-mode ultrasound images can be obtained after processing the echoes by the beamforming module 3. The processor 4 may then need to perform motion tracking and information association for the B-mode ultrasound images. In an example, the processor 4 can include a motion tracking preprocessing component 41 and a motion tracking post-processing component 42. Each B-mode ultrasound image can be displayed on the display device 5 after being transmitted through the motion tracking preprocessing component 41, and then users can carry out some operations or controls, such as selecting and/or adjusting a region of interest (ROI) area, on the B-mode ultrasound images. In the motion tracking postprocessing component 42, the motion tracking can be performed according to the selected ROI area, relevant parameter(s) can be calculated based on a motion tracking result, and the relevant parameter(s) can be displayed in association with the ultrasound image displayed on the display device 5. The users can select quantitative parameter(s) for displaying on a display interface.

In embodiments of this disclosure, the motion tracking postprocessing component 42 may be provided with an apparatus for associating detection information 421. The apparatus for associating detection information 421 can perform association processing on the detection information based on the motion tracking result of the B-mode ultrasound images, and display a processing result on different display areas of the display device 5. Alternatively, the apparatus for associating detection information 421 may read the ultrasound images from a storage medium, carry out corresponding processing, and display the processing result on different display areas of the display device 5.

In an embodiment, the apparatus for associating detection information 421 may include a motion tracking unit 4211, a tracking result calculation unit 4212 and a display configuration unit 4213.

The motion tracking unit 4211 can receive an image display type and a region of interest that are selected by an operator for images detected by the ultrasound system, disperse the region of interest into separated control points, and perform the motion tracking for the control points. Borders of the selected region of interest can be determined by the operator through manual tracing on a first frame or any frame of the images detected by the ultrasound system. The operator can adjust the shape, size and position of the region of interest as required.

The tracking result calculation unit 4212 can obtain position information of the control points in each image (i.e., each frame of the images, which can also be called as each image frame) from the motion tracking unit 4211 and calculate quantitative parameter information related to the images, where the quantitative parameter information may include quantitative parameter values.

The display configuration unit 4213 can configure each of the images detected by the ultrasound system and the position information of the control points in a first display area 51 of a display device 5 for displaying, configure the quantitative parameter information related to the images in a second display area 52 of the display device 5 for displaying, select an image model corresponding to the images detected by the ultrasound system according to the image display type, and configure the image model in a third display area 53 of the display device 5 for displaying. For configuring the quantitative parameter information related to the images in the second display area 52 of the display device 5 for displaying, the display configuration unit 4213 may calculate the quantitative parameter value for each segment of the region of interest (which can be referred to as an image segment below) based on a predetermined segment setting; the display configuration unit 4213 may then generate a quantitative parameter curve according to the quantitative parameter values of the respective image segment and time information of the images (i.e., the image frames) corresponding to the quantitative parameter values, where the generated quantitative parameter curve corresponds to the respective image segment (also, the quantitative parameter curve corresponds to a model segment described below). Here, the quantitative parameter value of each image segment may be substantially equal to a weight sum or an average value of the quantitative parameter values of the control points in the image segment. Besides, during the display of the image model, the display configuration unit 4213 may divide the image mode into several segments (which can be called as a model segment below) based on a segment number of the predetermined segment setting and fill each segment of the image model using different colors. During the generation of the quantitative parameter curve, the display configuration unit can make color coding on the quantitative parameter curve(s) corresponding to the respective segment, where the color of the quantitative parameter curve is consistent with that of its corresponding model segment. Moreover, when the operator selects the segment of the image model, the display configuration unit 4213 can highlight or hide the selected model segment and the quantitative parameter curve corresponding to the selected model segment on the display device 5, or the unselected model segment and its corresponding quantitative parameter curve can be hidden. Finally, a sign indicating a judgment result of the tracking result of each image segment can be displayed on the corresponding model segment of the image model by the display configuration unit 4213. In this embodiment, the third display area 53 may be located closer to the first display area 51 or the second display area 52.

The apparatus for associating detection information 421 can be one or more integrated chip(s) that may record programs for enabling the above-described functions.

Figure 2:
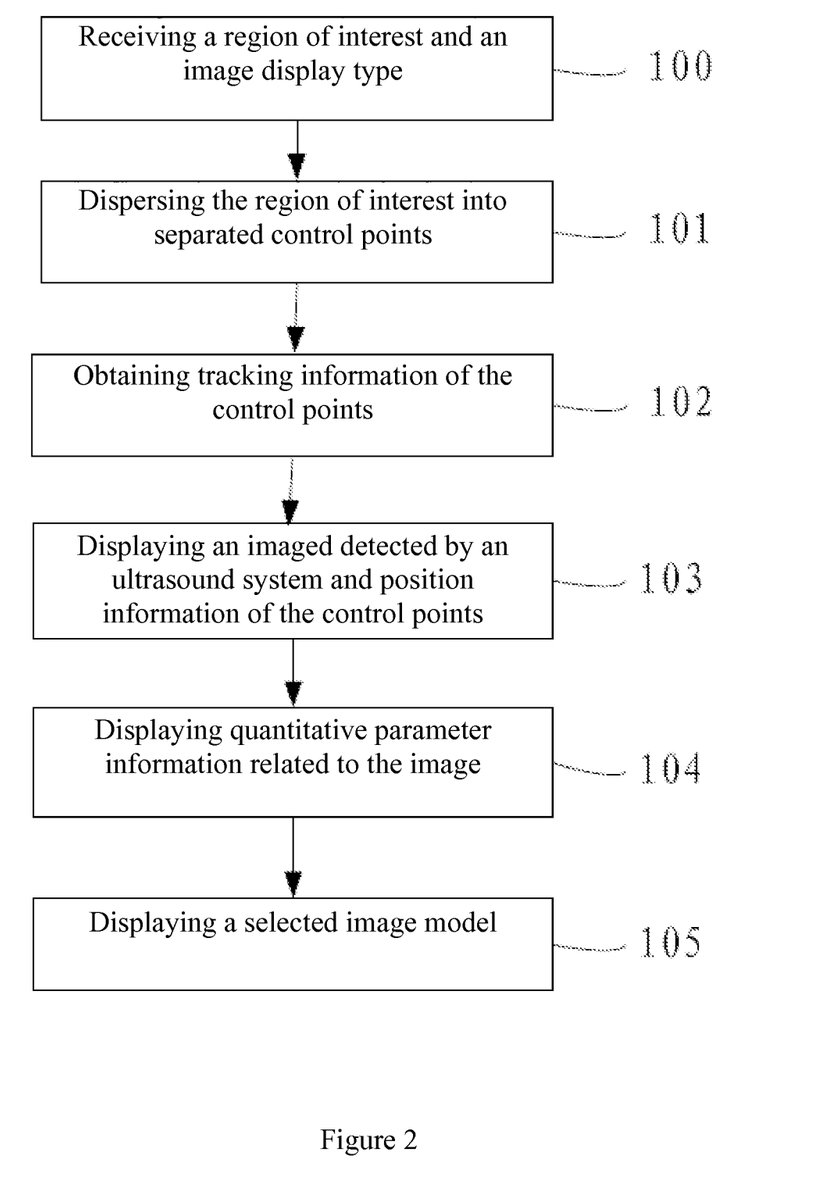
FIG. 2 is a flow chart illustrating a method for associating detection information of an ultrasound system according to an embodiment of this disclosure.

FIG. 2 illustrates a method for associating detection information based on the above-described ultrasound system. The method can include steps 100-105.

A region of interest and an image display type can be received in step 100.

The image display type and the region of interest that may be selected by an operator for ultrasound images displayed on the display device can be received in this step, where the image display type may be selected according to the displayed image(s). Borders of the selected region of interest can be determined by the operator through manual tracing on a first frame or any frame of the images detected by the ultrasound system. The operator can adjust the shape, the size and the position of the region of interest as required. The images detected by the ultrasound system can be acquired by the image acquisition module or read from a storage medium. In an embodiment, the images detected by the ultrasound system can be B-mode ultrasound images acquired by the image acquisition module. The image display type can be shown in the form of an icon or a pull-down menu on a display interface. The users can select the image display type for the B-mode ultrasound images as required, and each of the B-mode ultrasound images may then be displayed according to the selected image display type.

The region of interest can be dispersed into separated control points in step 101.

Tracking information of the control points can be obtained in step 102.

Block matching can be used for motion tracking of the control points, and the tracking information can be obtained thereafter. The tracking information can include position information of the control points in each image and quantitative parameter information related to the images, where the quantitative parameter information may include parameter(s) that may be related to the motion of the region of interest (such as velocity and/or displacement) or to the region of interest itself (such as strain and/or strain rate). The quantitative parameter information can not only include parameter values of one or more quantitative parameter(s) and time information for obtaining the quantitative parameter values, but also include the position information of the control points. The position information of the control points can be used for determining the image segment that the control points belong to.

Each image detected by the ultrasound system and the position information of the control points can be displayed in step 103.

Each image detected by the ultrasound system and the position information of the control points may be configured into a first display area of a display device for displaying.

The quantitative parameter information related to the images can be displayed in step 104.

The quantitative parameter information related to the images may be configured into a second display area of the display device for displaying. Specifically, the quantitative parameter values and time information for measuring the corresponding quantitative parameter values may be indicated in a two-dimensional coordinate system, so as to generate a time-varying quantitative parameter curve.

A selected image model can be displayed in step 105.

The image model corresponding to the images detected by the ultrasound system can be selected from an image model library according to the image display type, and the image model may be configured into a third display area of the display device for displaying.

In an embodiment, the steps 103, 104 and 105 may not be carried out following the sequence mentioned above. In various embodiments of this disclosure, these steps can be performed simultaneously or following a setting sequence. For example, the image model can be first displayed, and then the quantitative parameter curve can be displayed.

According to people's operating habits, graphics are easier to be found and perceived when compared with text. This is because graphics seem more intuitive, and there is no need for people to consider the meaning of the graphics. However, once seeing some text, people always need to comprehend the meaning of the text. Various embodiments of this disclosure can provide friendly user interface to users, by which the image display type can be intuitively indicated by a model graph on the display screen, so that the users can get the display type of the ultrasound image(s) according to the model and there is no need to search the text for the display type among numerous information on the display interface or try to figure out the meaning implied by the text.

In an embodiment, the ultrasound images (e.g., the region of interest) can be divided into several segments in accordance with a predetermined setting and each image segment may be associated with a corresponding quantitative parameter curve. The quantitative parameter curve can be generated using the following steps: dividing the region of interest into multiple segments based on the predetermined segment setting, calculating the quantitative parameter value of each segment of the region of interest, and generating the quantitative parameter curve that is corresponding to the image segment according to the quantitative parameter values of each image segment and the time information of the corresponding image frames. The image model can also be divided into several segments based on a segment number of the predetermined segment setting during the display of the image model.

In another embodiment, in order to highlight the association between the quantitative parameter and the segment of the ultrasound images, different colors can be filled in each segment of the image model during the display of the image model; color coding may be performed for the quantitative parameter curve corresponding to the respective segment (both the image segment and the model segment) during the generation of the quantitative parameter curve. Here, the color of the quantitative parameter curve is consistent with that of its corresponding model segment.

Since the color of the quantitative parameter curve is the same as that of the corresponding segment in the image model, it can be clearly known which quantitative parameter curve may correspond to which segment of the image model. After that, according to the consistency between the image model and the displayed ultrasound image, it can be clearly known which quantitative parameter curve may correspond to which segment of the ultrasound image that is actually displayed here, thereby associating the image information with the quantitative parameter information.

For convenience of observation, the third display area may be closer to the first display area or the second display area.

When the operator selects the segment of the image model, the apparatus for associating detection information of this disclosure can highlight or hide both the model segment selected by the operator and the quantitative parameter curve corresponding to the selected model segment. In an alternative embodiment, the unselected model segment and its corresponding quantitative parameter curve can be hidden.

In addition, the apparatus for associating detection information can also obtain a judgment result of the tracking result of each image segment, and the sign corresponding to the judgment result can be displayed on the corresponding segment of the image model.

Cardiac motion tracking is described below as an example for the above-described apparatus and method.

First, the ultrasound system may obtain a B-mode echocardiography, where the B-mode echocardiography can be acquired by the image acquisition module or read from the storage medium. The echocardiography may then be displayed on the display device after the processing of the motion tracking preprocessing component of the processor. By usage of a button indicating a view type, the user can select, according to the image type, a cardiac view type for a currently loaded image on an operation interface of the display device, so that the image display type can be selected in this case. The ROI (i.e., region of interest) can then be inputted for motion tracking on the loaded image of a first frame or any frame, where the border of the ROI can be manually traced and the ROI is generated based on the user input. The user can also adjust the generated ROI; for instance, the shape, the position and the size of the ROI can be adjusted. After finishing the input and the adjustment of the ROI, the user may click on a tracking start button, and the motion tracking postprocessing component of the processor may begin to recognize and track the motion of the ROI automatically. For the motion tracking, the ROI can be dispersed into several control points, and the motion of the control points can be tracked using block matching so as to obtain the position of the control points on each frame of the images. During the tracking, the system may display a progress bar showing the current tracking; after the tracking, the system may play the tracking result in which deformation and displacement of the ROI can be reconstructed according to the position of the control points on each image frame, where a reconstructed result may be displayed on the corresponding image. During playback of the motion tracking, the user can determine the accuracy of the tracking result through visual inspection. The system may automatically enter into a quantitative parameter display interface after finishing the playback of the tracking result, where the quantitative parameter can be parameter(s) related to the motion of the ROI (such as velocity and/or displacement) or parameter(s) related to the ROI itself (such as strain and/or strain rate). At this point, the user is required to determine whether the replayed tracking result is accurate. In the case where the tracking result is deemed to be inaccurate, the user can be allowed to reload another image or a new ROI can be inputted and adjusted again on the currently loaded image. In the case where the tracking result is accepted, the user can be allowed to replay the tracking result so as to observe the motion of the ROI. Besides, the user can select his interested quantitative parameter for displaying on the parameter display interface. The selected quantitative parameter and its related information can be recorded into a bull's-eye figure, and a related report can be generated according to the image type, the quantitative parameter and the bull's-eye figure.

The display device of the ultrasound system may also include a display window for displaying a current frame image and several slider(s), pull-down menu(s) and option button(s). In the process of selecting the image display type, the user can select the name of the view type through the pull-down menu and/or the option button according to the view type indicated by the frame image in the display window. After the view type is selected, one cardiac segment model can be displayed within the display window for indicating the view type. In the process of selecting the ROI, input devices such as a mouse or a trackball can be used to trace the border of the ROI in the display window for displaying the current frame (i.e., the current ultrasound image). After the border is determined, the ROI can be generated based on the user input. The shape, the size and the position of the ROI can be adjusted, in which case the ROI and/or its border can be dragged by the input device such as the mouse or the trackball, or the ROI can be adjusted by the button or the slider on the display interface. The user can then click on the tracking start button so as to make the system enter into the motion tracking process for the ROI after finishing the adjustment. The progress bar can be displayed during the tracking, while the motion tracking result can be replayed after the tracking.

When the motion tracking and the quantitative parameter calculations are finished, a calculation result can be displayed in a corresponding area on the display device. The display interface may include a tracking result display area (i.e., the first display area), a quantitative parameter display area (i.e., the second display area and the third display area) and an integrative information display area. The tracking result display area can be used for displaying the motion tracking result of the selected ROI in the images at different time instants. The ROI can be divided into several small areas or segments so as to distinguish different areas of a heart. The tracking result display area can include an electrocardiosignal display subarea for indicating the time information of the current frame. The echocardiography and the motion tracking result of the ROI can be dynamically replayed in the tracking result display area. The quantitative parameter display area may include at least one quantitative parameter curve related to the current image (displayed within the second display area), the name of the quantitative parameter shown by the curve, and a schematic diagram for a cardiac segment model (displayed within the third display area). The schematic diagram for a cardiac segment model can be located freely within the display window; for instance, it can be located within the display area of the current frame image. A chart in which one coordinate axis stands for time and the other coordinate axis stands for the numerical value of the quantitative parameter can be used in the quantitative parameter display area, where the magnitude of the quantitative parameter at each time instant can be represented by the curve within the chart. The quantitative parameter display area can also include a time node related to a time phase of the heart; for example, the position of an R peak of the ECG can be used as the time node indication. The integrative information display area can display global information (e.g., ejection fraction) related to the currently displayed view. The schematic diagram for the cardiac segment model may be required to clearly indicate the current cardiac view type and identify different cardiac segments with different colors, where the model segment is distributed corresponding to the segment of the cardiac image within the image area. In the quantitative parameter display area, the color of the quantitative parameter curve is consistent with that of its corresponding segment of the cardiac segment model. The schematic diagram for the cardiac segment model can not only establish correspondence between the quantitative parameter curve and the segment of the ROI of the cardiac image, but also provide highlighting display for the cardiac view that is being analyzed currently.

Figure 3:
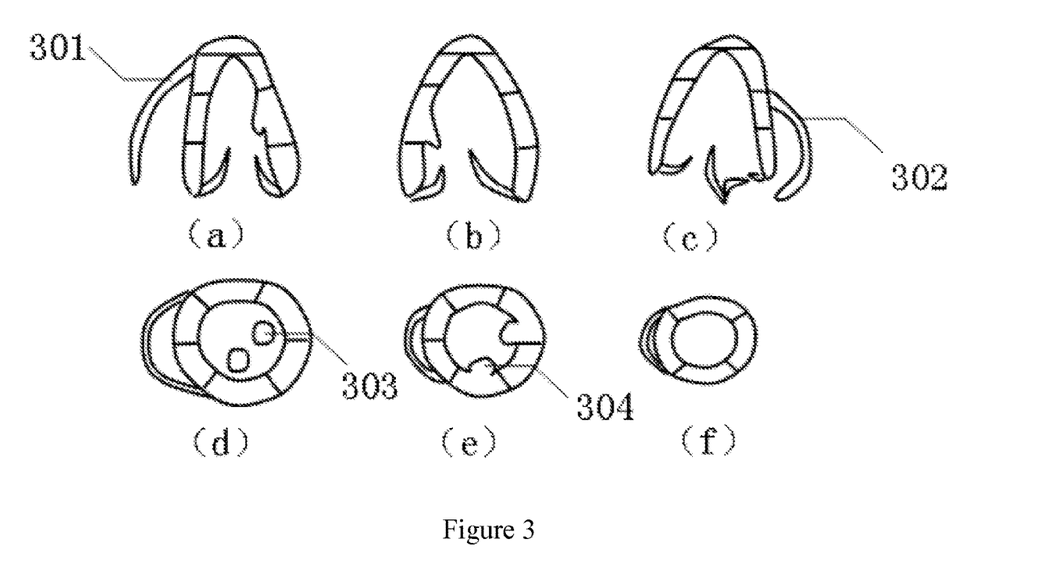
FIG. 3 is a schematic diagram illustrating view types of a heart according to an application example of this disclosure.

The schematic diagram for the cardiac segment model can be generated by selecting the cardiac view type for the currently loaded image on the operation interface. The size or the form of the schematic diagram for the cardiac segment model can be predetermined within the ultrasound system. As shown in FIG. 3, the predetermined cardiac segment models shown in the quantitative parameter display area respectively correspond to different cardiac view types. Here, the schematic diagram for the cardiac segment model can directly indicate the current cardiac view type as a whole. FIG. 3(*a*) is a cardiac four-chamber view, FIG. 3(*b*) is a cardiac two-chamber view, FIG. 3(*c*) is a cardiac three-chamber view, FIG. 3(*d*) is a mitral valve level view of a heart, FIG. 3(*e*) is a papillary muscle level view of a heart, and FIG. 3(*f*) is an apical level view of a heart. It is clear that those different schematic diagrams for the cardiac segment model are significantly different from each other. For example, FIG. 3(*a*) can be distinguished to be the cardiac four-chamber view using the position of a right ventricular wall 301, FIG. 3(*b*) can be distinguished to be the cardiac two-chamber view, FIG. 3(*c*) can be determined to be the cardiac three-chamber view using the position of a right ventricular wall 302, FIG. 3(*d*) can be determined to be a short-axis mitral valve level view of a heart using features of a chordate tendineae 303, FIG. 3(*e*) can be determined to be a short-axis papillary muscle level view of a heart using features of papillary muscle 304, and FIG. 3(*f*) can be distinguished to be a short-axis apical level view of a heart. In each schematic diagram for the cardiac segment model, a common name of the view type that may be represented by the schematic diagram for the cardiac segment model can be used to identify the corresponding schematic diagram. The schematic diagram for the cardiac segment model can be divided into several segments according to a cardiac 17-segment model or a cardiac 16-segment model, and the obtained cardiac segments can be identified using different colors. Predetermined colors can be applied to different cardiac segments, or the user can manually input the color for the respective cardiac segment. The colors between different cardiac segments are required to be greatly distinct with each other. After the cardiac segments are identified with colors, the color(s) of each model segment or several model segments on the schematic diagram for the cardiac segment model is/are required to be consistent with that/those of the quantitative parameter curve corresponding to the cardiac segment(s). The common name of the respective cardiac segment can be used as its identification in the schematic diagram for the cardiac segment model. When the user selects any cardiac segment in the schematic diagram for the cardiac segment model, the selected cardiac segment as well as its corresponding quantitative parameter curve can be highlighted.

Figure 4:
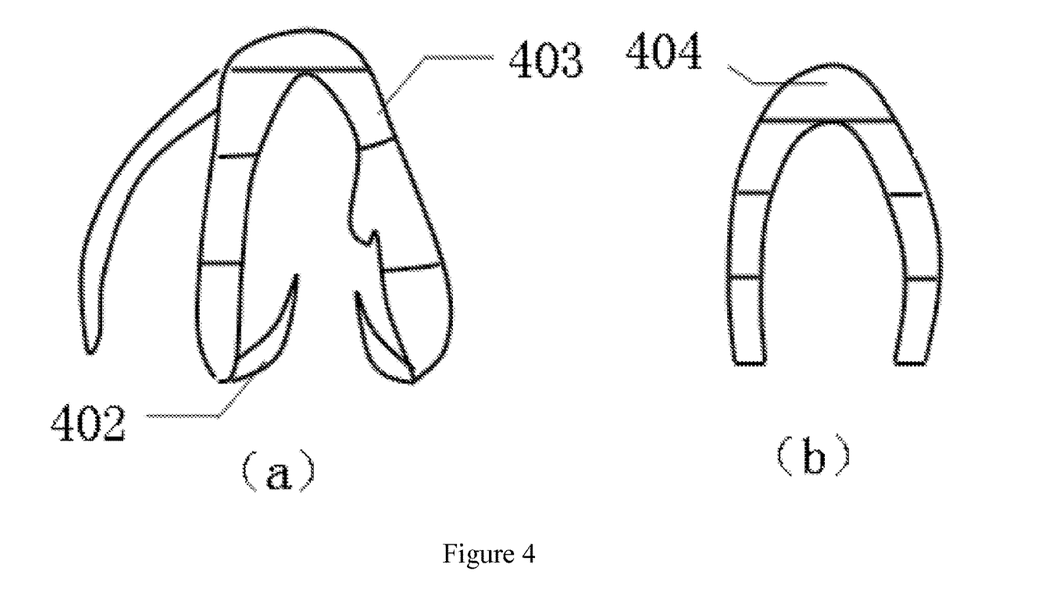
FIG. 4 is a schematic diagram illustrating different display modes for a segment model of the cardiac four-chamber view in FIG. 3.

Other forms can be used for the schematic diagrams for the cardiac segment model (which indicate the cardiac view) in the quantitative parameter display area. Taking the cardiac four-chamber view as an example, a left ventricle of a heart includes a myocardial wall and an interventricular septum 403 as shown in FIG. 4(a). Here, the interventricular septum and the myocardial wall can be respectively divided into seven or six segments according to the cardiac 17-segment model or the cardiac 16-segment model, where different cardiac segments are identified by different colors, and the colors between different cardiac segments are required to be distinct with each other. After the cardiac segment is identified with color, the color(s) of each model segment or several model segments on the schematic diagram for the cardiac segment model is/are required to be consistent with that/those of the quantitative parameter curve corresponding to the cardiac segment(s). The cardiac four-chamber segment model can also include a right ventricular wall, and the position of the right ventricular wall can indicate that the current view type is the cardiac four-chamber view. The cardiac four-chamber segment model can also include a mitral valve 402, and the position of the mitral valve 402 may indicate the mitral valve level. There can be other forms of schematic diagrams for the cardiac segment model illustrating the cardiac view. FIG. 4(b) is a schematic diagram for the cardiac segment model illustrating another cardiac four-chamber view. In this figure, an interventricular septum and a ventricular wall of a left ventricle can be identified by an arc-shaped structure 404 or any other suitable shapes, and the current view type can be identified by its common name. The left ventricle includes a myocardial wall and the interventricular septum. Here, the interventricular septum and the myocardial wall can be respectively divided into seven or six segments according to the cardiac 17-segment model or the cardiac 16-segment model. Different cardiac segments may be identified by different colors, their common names or a combination of these two identifying methods.

In the quantitative parameter display area, the schematic diagram for the cardiac segment model for the cardiac view can be generated according to the shape and/or the size of the ROI on the display interface of the tracking result; for instance, the ROI of the current image can be enlarged, stretched or deformed in other ways to obtain the schematic diagram for the cardiac segment model for the cardiac view. The schematic diagram for the cardiac segment model for the cardiac view can be respectively divided into several segments according to the cardiac 17-segment model or the cardiac 16-segment model. Different cardiac segments may be identified by different colors, their common names or a combination of these two identifying methods. The schematic diagram for the cardiac segment model for the cardiac view can remain consistent with the ROI of the current image displayed in the tracking result display area.

When the user selects the view type, the schematic diagram for the cardiac segment model can be obtained by loading a predetermined image in the ultrasound system according to the user's selection. Alternatively, the schematic diagram for the cardiac segment model can be generated based on the shape and/or the size of the ROI on the display interface of the tracking result. The schematic diagram for the cardiac segment model can display a real-time distribution of the quantitative parameter(s) within the ROI on the current display interface. In an embodiment, the distribution of the quantitative parameter within the ROI can be displayed in real time on the schematic diagram for the cardiac segment model as follows: searching for a corresponding color in a color table according to the quantitative parameter value of a point within the ROI, and filling the color into a position corresponding to this point on the schematic diagram for the cardiac segment model. The schematic diagram for the cardiac segment model can also display the distribution of the quantitative parameter(s) of the cardiac segment on the current display interface in real time. In an embodiment, the distribution of the quantitative parameter of the cardiac segment on the current display interface can be displayed in real time on the schematic diagram for the cardiac segment model as follows: searching for a corresponding color in a color table according to the quantitative parameter value of the cardiac segment, and performing color filing for a corresponding cardiac segment on the schematic diagram for the cardiac segment model.

Figure 5:
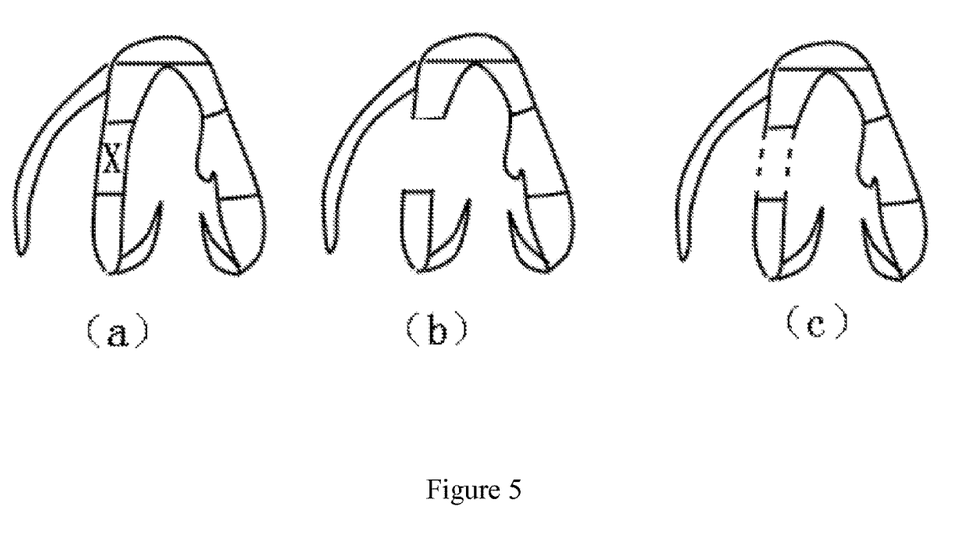
FIG. 5 is a schematic diagram illustrating identification methods for indicating whether a tracking result of a certain segment of a cardiac segment model is effective according to an application example of this disclosure.

The schematic diagram for the cardiac segment model displayed within the quantitative parameter display area can also indicate whether the tracking result of a segment during the cardiac motion tracking is effective. An apparent sign can be used to indicate whether the motion tracking of the cardiac segment is successful. For example, a sign "X" indicating a mistake as shown in FIG. 5(a), some text such as "WRONG" and/or "UNACCEPTABLE" to indicate a mistake, or a predetermined color such as black can be used to indicate unsuccessful motion tracking for the cardiac segment. Alternatively, the segment determined by the system or the user to have successful tracking can be displayed, while the cardiac segment having unsuccessful motion tracking can be hidden (as shown in FIG. 5(b)) or its border can be described in other lines such as dashed lines (as shown in FIG. 5(c)).

The schematic diagram for the cardiac segment model can be dragged, enlarged or stretched within the display interface by the user. The schematic diagram for the cardiac segment model can be dragged to any position on the display interface so as to get an optimal display effect. The schematic diagram for the cardiac segment model can be enlarged or reduced so that the user can observe some detailed change information about the myocardial motion. The schematic diagram for the cardiac segment model can be stretched for an optimal effect.

The cardiac segment can be selectively displayed on the schematic diagram for the cardiac segment model. The user can select to display one or more cardiac segment(s) and hide the remaining cardiac segment(s). The quantitative parameter display area can display or hide the quantitative parameter of the corresponding cardiac segment according to the user selection.

In this disclosure, the information obtained in the ultrasound system can be displayed on the display screen in an intuitive mode through the above-described methods and apparatuses. Because the information obtained in the ultrasound system is identified through establishing association between the quantitative parameter curve and the color, it can be great help for the user to effectively perceive various information, thereby reducing the possible of wrong perception brought about by other modes (e.g., by text).

This disclosure is described above as detailed illustrations with reference to specific implementations, while this disclosure should not be limited to these illustrations. For those of ordinary skills in the art, various conclusions or equivalents may be made without departing from the concept of this disclosure, while such conclusions or equivalents should be deemed to be included within the scope of this disclosure.

The invention claimed is:

1. A method for associating detection information of an ultrasound system, comprising:
   receiving a region of interest and an image display type that are selected by an operator for images detected by the ultrasound system;
   performing motion tracking for the region of interest and obtaining tracking information, wherein the tracking information comprises position information of the region of interest in each image and quantitative parameter information related to the images, wherein the quantitative parameter information comprises quantitative parameter values;
   displaying each image and the position information of the region of interest corresponding to each image in a first display area of a display device;
   displaying the quantitative parameter information related to the images in a second display area of the display device, wherein portions of the quantitative parameter information are displayed as one or more time-varying quantitative parameter curves; and
   displaying a cardiac segment model for at least one image of the images in a third display area of the display device, wherein the cardiac segment model is divided into multiple model segments, wherein at least one model segment of the multiple model segments corresponds to at least one respective time-varying quantitative parameter curve of the one or more time-varying quantitative parameter curves displayed in the second display area, wherein the at least one model segment in the third display area is selectable by the operator to selectively display, highlight, and/or hide a respective time-varying quantitative parameter curve in the second display area, wherein the first display area, the second display area, and the third display area are separate display areas for respectively displaying the images and corresponding position information, the quantitative parameter information, and the cardiac segment model separately.

2. The method of claim 1, wherein displaying the quantitative parameter information related to the images in the second display area of the display device comprises:
   dividing the region of interest into multiple image segments based on a predetermined segment setting;
   calculating the quantitative parameter value for each image segment of the region of interest;
   generating the one or more time-varying quantitative parameter curves corresponding to said each image segment according to the quantitative parameter values of said each image segment and time information of the images corresponding to the quantitative parameter values; and
   displaying the one or more time-varying quantitative parameter curves in the second display area.

3. The method of claim 1, wherein each model segment of the cardiac segment model in the third display area is displayed using a different color, and wherein at least one time-varying quantitative parameter curve in the second display area is displayed using the color of the corresponding model segment in the third display area.

4. The method of claim 3, further comprising:
   receiving a segment selection operation on the cardiac segment model by the operator, and highlighting or hiding a selected model segment and the time-varying quantitative parameter curve corresponding to the selected model segment; or
   receiving a segment selection operation on the cardiac segment model by the operator, and hiding an unselected model segment and the time-varying quantitative parameter curve corresponding to the unselected model segment.

5. The method of claim 3, further comprising:
   obtaining a judgment result on a tracking result of said each model segment, and displaying a sign corresponding to the judgment result on a corresponding model segment of the cardiac segment model.

6. The method of claim 1, further comprising:
   dispersing the region of interest into separated control points, and performing the motion tracking for the control points, wherein the position information of the region of interest comprises position information of the control points.

7. An apparatus for associating detection information of an ultrasound system, comprising:
   a motion tracking unit for receiving a region of interest and an image display type that are selected by an operator for at least one image of a plurality of images detected by the ultrasound system, and performing motion tracking for the region of interest for the plurality of images;
   a tracking result calculation unit for:
      obtaining position information of the region of interest in each image of the plurality of images from the motion tracking unit; and
      calculating quantitative parameter information related to the plurality of images, wherein the quantitative parameter information comprises quantitative parameter values; and
   a display configuration unit for:
      displaying each image and the position information of the region of interest corresponding to each image in a first display area of a display device;
      displaying the quantitative parameter information related to each image in a second display area of the display device, wherein portions of the quantitative parameter information are displayed as one or more time-varying quantitative parameter curves; and
      displaying a cardiac segment model for at least one image of the plurality of images in a third display area of the display device, wherein the cardiac segment model is determined based on the selected image display type, wherein the cardiac segment model is divided into multiple model segments, wherein each model segment of the multiple model segments corresponds to at least one respective time-varying quantitative parameter curve of the one or more time-varying quantitative parameter curves displayed in the second display area, wherein each model segment of the cardiac segment model in the third display area is selectable by the operator to selectively display, highlight, and/or hide the respective at least one time-varying quantitative parameter curve in the second display area, and wherein the first display area, the second display area, and the third display area are separate display areas for displaying the plurality of images and corresponding position information, the quantitative parameter information, and the cardiac segment model separately.

8. The apparatus of claim 7, wherein the display configuration unit is configured to display the quantitative parameter information related to the plurality of images in the second display area of the display device by:
  dividing the region of interest into multiple image segments based on a predetermined segment setting;
  calculating the quantitative parameter value for each image segment of the region of interest;
  generating the one or more time-varying quantitative parameter curves corresponding to said each image segment according to the quantitative parameter values of said each image segment and time information of the plurality of images corresponding to the quantitative parameter values; and
  displaying the one or more time-varying quantitative parameter curves in the second display area.

9. The apparatus of claim 8, wherein the motion tracking unit disperses the region of interest into multiple control points and performs the motion tracking for the control points; the position information of the region of interest comprises position information of the control points.

10. The apparatus of claim 9, wherein the quantitative parameter value of said each image segment is equal to a weight sum or an average value of the quantitative parameter values of the control points contained in said each image segment.

11. The apparatus of claim 7, wherein the display configuration unit displays each model segment of the cardiac segment model in the third display area using a different color and displays at least one time-varying quantitative parameter curve in the second display area using the color of the corresponding model segment in the third display area.

12. The apparatus of claim 11, wherein the display configuration unit displays a sign that corresponds to a judgment result of a tracking result of said each model segment on a corresponding one of the multiple model segments of the cardiac segment model based on the position information.

13. The apparatus of claim 7, wherein the display configuration unit highlights or hides a selected model segment and the time-varying quantitative parameter curve corresponding to the model segment selected by the operator on the cardiac segment model; or
  the display configuration unit hides an unselected model segment and the time-varying quantitative parameter curve corresponding to the unselected model segment.

14. The apparatus of claim 7, wherein the plurality of images detected by the ultrasound system are cardiac images, and the quantitative parameter information comprises velocity, displacement, strain and/or strain rate.

15. The apparatus of claim 7, wherein the position information of the region of interest comprises position information of a border of the region of interest.

16. The apparatus of claim 7, wherein the cardiac segment model directly indicates a current cardiac view type.

17. The apparatus of claim 7, wherein the cardiac segment model includes a schematic representation of a cardiac four-chamber view, a cardiac two-chamber view, a cardiac three-chamber view, a mitral valve level view of a heart, a papillary muscle level view of a heart, and an apical level view of a heart.

18. The apparatus of claim 7, wherein different model segments are identified with different colors.

19. The apparatus of claim 7, wherein a size or form of the cardiac segment model is predetermined by the ultrasound system.

20. The apparatus of claim 7, wherein the tracking result calculation unit is further configured for indicating whether a tracking result of a specific segment of the multiple model segments is effective.

21. The apparatus of claim 7, wherein the tracking result calculation unit is further configured for obtaining global information related to the plurality of images, the global information including an ejection fraction.

22. The apparatus of claim 21, wherein the display configuration unit displays the global information related to the plurality of images in a fourth display area of the display device, the fourth display area being separate from the first, second and third display areas.

23. The apparatus of claim 7, wherein the plurality of images, the quantitative parameter information, and the cardiac segment model are correlated.

24. An ultrasound system, comprising:
  an image acquisition module comprising a transmission module for emitting an ultrasonic wave by an ultrasound probe and a receiving module for receiving echo signals;
  a beamforming module for processing the echo signals to obtain B-mode ultrasound images; and
  an apparatus for associating detection information that performs association processing on the detection information based on the B-mode ultrasound images;
  wherein the apparatus for associating detection information comprises:
  a motion tracking unit for receiving a region of interest and an image display type that are selected by an operator for the B-mode ultrasound images, and performing motion tracking for the region of interest;
  a tracking result calculation unit for obtaining position information of the region of interest in each of the B-mode ultrasound images from the motion tracking unit and calculating quantitative parameter information related to the B-mode ultrasound images; the quantitative parameter information comprises a quantitative parameter value; and
  a display configuration unit for:
    displaying each B-mode ultrasound image and the position information of the region of interest corresponding to said each B-mode ultrasound image in a first display area of a display device;
    displaying the quantitative parameter information related to the B-mode ultrasound images in a second display area of the display device, wherein portions of the quantitative parameter information are displayed as one or more time-varying quantitative parameter curves; and
    displaying a cardiac segment model for at least one of the B-mode images in a third display area of the display device, wherein the cardiac segment model is divided into multiple model segments, wherein at least one model segment of the multiple model segments corresponds to at least one respective time-varying quantitative parameter curve of the one or more time-varying quantitative parameter curves displayed in the second display area, wherein the at least one model segment in the third display area is selectable by the operator to selectively display, highlight, and/or hide the respective at least one time-varying quantitative parameter curve in the second display area, and wherein the first display area, the second display area, and the third display area are separate display areas for respectively displaying each B-mode ultrasound image and corresponding position information, the quantitative parameter information, and the cardiac segment model separately.

25. The ultrasound system of claim 24, wherein the cardiac segment model directly indicates a current cardiac view type.

26. The ultrasound system of claim 24, wherein the cardiac segment model includes a schematic representation of a cardiac four-chamber view, a cardiac two-chamber view, a cardiac three-chamber view, a mitral valve level view of a heart, a papillary muscle level view of a heart, and an apical level view of a heart.

27. The ultrasound system of claim 24, wherein the tracking result calculation unit is further configured to indicate whether a tracking result of a specific segment of the multiple model segments is effective.

28. The ultrasound system of claim 24, wherein the tracking result calculation unit is further configured to obtain global information related to the B-mode ultrasound images, the global information including an ejection fraction.

29. The ultrasound system of claim 28, wherein the display configuration unit displays the global information related to the B-mode model images in a fourth display area of the display device, the fourth display area being a display area separate from the first, second and third display areas.

\* \* \* \* \*